(12) United States Patent
Park et al.

(10) Patent No.: US 11,139,072 B2
(45) Date of Patent: Oct. 5, 2021

(54) THREE-DIMENSIONAL MEDICAL IMAGE GENERATION

(71) Applicant: INTERNATIONAL BUSINESS MACHINES CORPORATION, Armonk, NY (US)

(72) Inventors: Sun Young Park, San Diego, CA (US); Dustin Michael Sargent, San Diego, CA (US); James G. Thompson, Escondido, CA (US)

(73) Assignee: International Business Machines Corporation, Armonk, NY (US)

( * ) Notice: Subject to any disclaimer, the term of this patent is extended or adjusted under 35 U.S.C. 154(b) by 0 days.

(21) Appl. No.: 16/703,187

(22) Filed: Dec. 4, 2019

(65) Prior Publication Data
US 2021/0174938 A1 Jun. 10, 2021

(51) Int. Cl.
*G16H 30/40* (2018.01)
*G06T 15/00* (2011.01)
*G06K 9/62* (2006.01)

(52) U.S. Cl.
CPC .......... *G16H 30/40* (2018.01); *G06K 9/6267* (2013.01); *G06T 15/00* (2013.01); *G06K 2209/05* (2013.01); *G06T 2210/41* (2013.01)

(58) Field of Classification Search
CPC .. G16H 30/40; G06K 9/6267; G06K 2209/05; G06T 15/00; G06T 2210/41
See application file for complete search history.

(56) References Cited

U.S. PATENT DOCUMENTS

| 8,489,407 B2 | 7/2013 | Bradley |
| 9,009,653 B2 | 4/2015 | Padmalata |

(Continued)

FOREIGN PATENT DOCUMENTS

| EP | 3447731 A1 | 2/2019 |
| KR | 101898575 B1 | 9/2018 |

(Continued)

OTHER PUBLICATIONS

G Kim, et al., "Feasibility study of deep convolutional generative adversarial networks to generate mammography images", SPIE Medical Imaging, 2018, 7 pages, Houston, Texas, US, DOI: 10.1117/12.2293046.

(Continued)

*Primary Examiner* — Haixia Du
(74) *Attorney, Agent, or Firm* — Caleb D. Wilkes (57) ABSTRACT

An embodiment of the invention may include a method, computer program product and computer system for three-dimensional medical image generation. The method, computer program product and computer system may include computing device which may receive a first three-dimensional medical image of a first patient from a first period of time, a two-dimensional medical image of the first patient from a second period of time and a plurality of three-dimensional medical images for a plurality of second patients. The computing device may input the three-dimensional medical image of the first patient, the two-dimensional medical image of the first patient and the plurality of three-dimensional medical images for a plurality of second patients into a generative adversarial network (GAN). The computing device may generate a synthetic three-dimensional medical image for the first patient based on the two-dimensional medical image from the second period of time utilizing the GAN.

20 Claims, 6 Drawing Sheets

(56) References Cited

U.S. PATENT DOCUMENTS

| | | | |
|---|---|---|---|
| 9,456,797 | B2 | 10/2016 | Ruth |
| 2009/0178021 | A1 | 7/2009 | Alluri |
| 2014/0172512 | A1 | 6/2014 | Chandra |
| 2019/0087730 | A1 | 3/2019 | Saito |
| 2019/0261945 | A1* | 8/2019 | Funka-Lea ............. A61B 8/145 |

FOREIGN PATENT DOCUMENTS

| | | |
|---|---|---|
| WO | 2017223560 A1 | 12/2017 |
| WO | 2018206504 A1 | 11/2018 |
| WO | 2018232388 A1 | 12/2018 |

OTHER PUBLICATIONS

Guan, et al., "Breast cancer detection using synthetic mammograms from generative adversarial networks in convolutional neural networks", The Fourteenth International Workshop on Breast Imaging, 2018, Atlanta, Georgia, US, Retrieved from the Internet: <URL: https://doi.org/10.1117/12.2318100>.

Hologic, Inc., "System and method for generating a 2D image using mammography and/or tomosynthesis image data", Nov. 26, 2012 [accessed on Dec. 4, 2019], 24 pages, Retrieved from the Internet: <URL: https://patents.justia.com/patent/10008184>.

Kim, et al., "Feasibility study of deep convolutional generative adversarial networks to generate mammography images", Proc. SPIE 10577, Medical Imaging 2018: Image Perception, Observer Performance, and Technology Assessment, Mar. 7, 2018 [accessed on Jun. 12, 2019], 7 pages, Houston, Texas, US, Retrieved from the Internet: <URL: https://doi.org/10.1117/12.2293046>.

Korkinof, et al., "High-Resolution Mammogram Synthesis using Progressive Generative Adversarial Networks", Jul. 19, 2018, 19 pages, Retrieved from the Internet: <URL: https://arxiv.org/abs/1807.03401>.

Mell, et al., "The NIST Definition of Cloud Computing", National Institute of Standards and Technology, Special Publication 800-145, Sep. 2011, 7 pages.

Nguyen, et al., "Dual Discriminator Generative Adversarial Nets", D31st Conference on Neural Information Processing Systems (NIPS 2017), Sep. 12, 2017 [accessed on Dec. 4, 2019], 11 pages, Long Beach, CA, USA, Retrieved from the Internet: <URL: https://arxiv.org/pdf/1709.03831.pdf?>.

Nie, et al., "Medical Image Synthesis with Context-Aware Generative Adversarial Networks", Dec. 16, 2016, 12 pages, Retrieved from the Internet: <URL: https://arxiv.org/abs/1612.05362>.

S Kim, et al., "ICADx: Interpretable computer aided diagnosis of breast masses" May 23, 2018, Image and Video Systems Lab., School of Electrical Engineering, 10 pages, KAIST, South Korea, Retrieved from the Internet: <URL: https://arxiv.org/abs/1805.08960>.

Van Schie, et al., "Generating Synthetic Mammograms From Reconstructed Tomosynthesis Volumes", IEEE Transactions on Medical Imaging, Dec. 2013 [accessed on Dec. 2, 2019], pp. 2322-2331, vol. 32, No. 12, DOI: 10.1109/TMI.2013.2281738, Retrieved from the Internet: <URL: https://ieeexplore.ieee.org/stamp/stamp.jsp?tp=&arnumber=6601020>.

Wu, et al., "Conditional Infilling GANs for Data Augmentation in Mammogram Classification." Aug. 24, 2018, 8 pages, Retrieved from the Internet: <URL: https://arxiv.org/abs/1807.08093>.

Zhu, et al., "Learning Adversarial 3D Model Generation with 2D Image Enhancer, NYU Multimedia and Visual Computing Lab", The Thirty-Second AAAI Conference on Artificial Intelligence (AAAI-18), [accessed on Dec. 2, 2019], pp. 7615-7622, Retrieved from the Internet: <URL: https://www.aaai.org/ocs/index.php/AAAI/AAAI18/paper/download/16064/16360>.

* cited by examiner

THREE-DIMENSIONAL MEDICAL IMAGE GENERATION

BACKGROUND

The present invention relates generally to a method, system, and computer program for three-dimensional medical image generation. More particularly, the present invention relates to a method, system, and computer program for generating a digital breast tomosynthesis image corresponding to prior full-field digital mammography images.

Medical imaging includes techniques and processes to create visual representations of the interior of a body for clinical analysis and medical intervention. Further, medical imaging seeks to provide a visual representation of the functions of some organs or tissues. Medical imaging also seeks to reveal internal structures which may be hidden by skin and/or bones, as well as to diagnose and treat disease. Medical imaging has allowed the medical community to establish a database of normal anatomy and physiology enabling the identification of physiological abnormalities including indicators of disease.

BRIEF SUMMARY

An embodiment of the invention may include a method, computer program product and computer system for three-dimensional medical image generation. The method, computer program product and computer system may include computing device which may receive a three-dimensional medical image of a first patient from a first period of time, a two-dimensional medical image of the first patient from a second period of time and a plurality of three-dimensional medical images for a plurality of second patients. The computing device may input the three-dimensional medical image of the first patient, the two-dimensional medical image of the first patient and the plurality of three-dimensional medical images for a plurality of second patients into a generative adversarial network (GAN). The computing device may generate a synthetic three-dimensional medical image for the first patient based on the two-dimensional medical image from the second period of time utilizing the GAN. The computing device may input the synthetic three-dimensional medical image into a first discriminator of the GAN, wherein the first discriminator tries to discriminate between the synthetic three-dimensional medical image and the plurality of three-dimensional medical images from the plurality of second patients. The computing device may input the synthetic three-dimensional medical image into a second discriminator of the GAN, wherein the second discriminator creates a projected two-dimensional medical images corresponding to the synthetic three-dimensional medical image, wherein the second discriminator tries to discriminate between the projected two-dimensional medical images corresponding to the synthetic three-dimensional medical image and two-dimensional medical image of the first patient from a second period of time.

In embodiments of the invention, computing device may analyze the synthetic three-dimensional medical image of the first patient for one or more differences compared to the first three-dimensional medical image of the first patient. The computing device may annotate the three-dimensional medical image of the first patient with indicators indicating the differences between the first three-dimensional medical image of the first patient and the synthetic three-dimensional image of the first patient. The computing device may generate a report with a textual description of the detected differences. The computing device may display the synthetic three-dimensional medical image of the first patient and/or the report to a user via a user interface and/or the annotated three-dimensional medical image of the first patient.

BRIEF DESCRIPTION OF THE DRAWINGS

FIG. 1b illustrates example operating modules of the three-dimensional medical image generation program of FIG. 1a.

DETAILED DESCRIPTION

Embodiments of the present invention will now be described in detail with reference to the accompanying Figures.

The following description with reference to the accompanying drawings is provided to assist in a comprehensive understanding of exemplary embodiments of the invention as defined by the claims and their equivalents. It includes various specific details to assist in that understanding but these are to be regarded as merely exemplary. Accordingly, those of ordinary skill in the art will recognize that various changes and modifications of the embodiments described herein can be made without departing from the scope and spirit of the invention. In addition, descriptions of well-known functions and constructions may be omitted for clarity and conciseness.

The terms and words used in the following description and claims are not limited to the bibliographical meanings, but, are merely used to enable a clear and consistent understanding of the invention. Accordingly, it should be apparent to those skilled in the art that the following description of exemplary embodiments of the present invention is provided for illustration purpose only and not for the purpose of limiting the invention as defined by the appended claims and their equivalents.

It is to be understood that the singular forms "a," "an," and "the" include plural referents unless the context clearly dictates otherwise. Thus, for example, reference to "a component surface" includes reference to one or more of such surfaces unless the context clearly dictates otherwise.

Embodiments of the present invention provide a method, computer program, and computer system for generating a three-dimensional medical image. Currently, breast cancer is typically screened using either full-field digital mammography (FFDM), which is a form of two-dimensional medical imaging, or digital breast tomosynthesis (DBT), which is a form of three-dimensional medical imaging. Increasingly, DBT is replacing FFDM as the standard screening modality due to the increased sensitivity and specificity of DBT. Thus, it is becoming increasingly common for patients to have new exams performed with DBT and prior exams having been performed with FFDM. Medical professionals may need to compare newer three-dimensional screenings, e.g. DBT screenings, with older two-dimensional screenings, e.g. FFDM screening. This comparison of DBT to FFDM images can be difficult because FFDM projects the whole tissue volume into a two-dimensional image, which may cause calcifications, and lesions, etc. to overlap with normal areas of dense tissue. Thus, the tissue details that are visible in newer DBT images but obscured in prior FFDM images may lead to incorrect diagnoses. Embodiments of the present invention utilize a machine learning approach to synthesize prior DBT volumes from current DBT and prior FFDM images for the same patient. Specifically, embodiments of the present invention utilize a generative adversarial network (GAN) to generate a synthetic three-dimensional medical image, e.g. a synthetic DBT image, corresponding to one or more patient's past two-dimensional medical images. Thus, embodiments of the present invention may allow medical professionals to compare past medical images to current medical images more accurately.

Reference will now be made in detail to the embodiments of the present invention, examples of which are illustrated in the accompanying drawings, wherein like reference numerals refer to like elements throughout. Embodiments of the invention are generally directed to three-dimensional medical image generation.

Figure 1A:
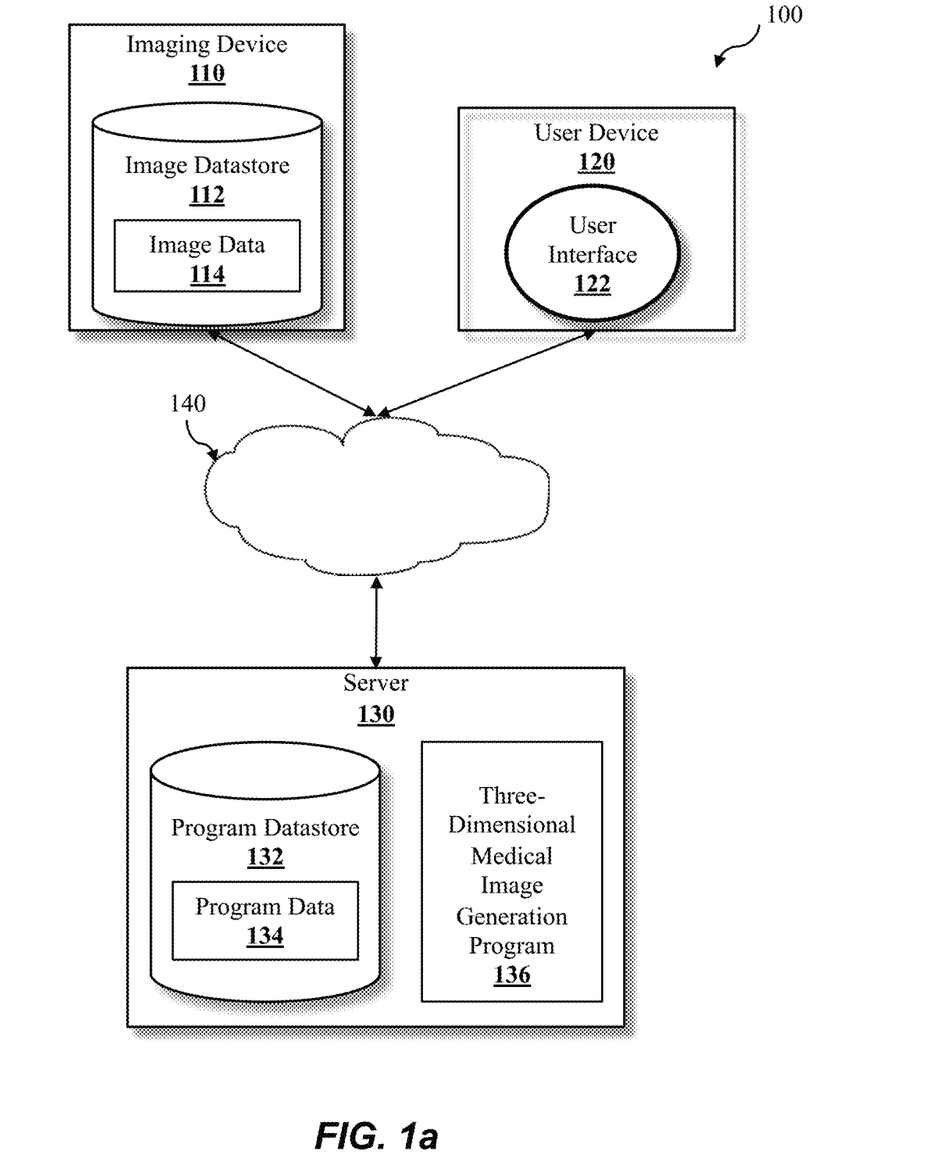
FIG. 1a illustrates a system for three-dimensional medical image generation, in accordance with an embodiment of the invention.

FIG. 1 illustrates a three-dimensional medical image generation system 100, in accordance with an embodiment of this invention. In an example embodiment, the three-dimensional medical image generation system 100 includes an imaging device 110, a user device 120, and a server 130 interconnected via a network 140.

In the example embodiment, the communication network 140 is the Internet, representing a worldwide collection of networks and gateways to support communications between devices connected to the Internet. The network 140 may include, for example, wired, wireless or fiber optic connections. In other embodiments, the network 140 may be implemented as an intranet, a local area network (LAN), or a wide area network (WAN), or a wired or wireless personal area network (PAN). In general, the network 140 can be any combination of connections and protocols that will support communications between the imaging device 110, the user device 120, and the server 130.

The imaging device 110 may include the image datastore 112. The imaging device 110 may be any device capable of capturing the image data 114. In an example embodiment, the imaging device 110 may be a medical imaging device employing imaging technology such as, but not limited to, tomosynthesis imaging, digital breast tomosynthesis (DBT), full-field digital mammography (FFDM), X-ray radiography, magnetic resonance imaging (MM), medical ultrasonography or ultrasound, endoscopy, elastography, tactile imaging, thermography, medical photography, photoacoustic imaging, electrocardiography, functional near-infrared spectroscopy (FNIR), magnetic particle imaging (MPI). In addition, the imaging device 110 may employ nuclear medicine functional imaging techniques, such as positron emission tomography (PET) and single-photon emission computed tomography (SPECT). The imaging device 110 may be any imaging device capable of capturing the image data 114 and sending the image data 114 to and from other computing devices, such as the user device 120, and the server 130 via the network 140. The image data 114 may include, but is not limited to, visual, audio, and/or textual data. The image data 114 may include any images of one or more parts of the body, including three-dimensional and two-dimensional images, captured by the imaging device 110 such as, but not limited to, digital breast tomosynthesis (DBT) images, full-field digital mammography (FFDM) images, X-rays, magnetic resonance images (Mills), ultrasounds, endoscopic images, elastography images, tactile images, thermography images, medical photographs, photoacoustic images, electrocardiographs, functional neuroimages, magnetic particle imaged (MPIs), positron emission tomography (PET) scans, and single-photon emission computed tomography (SPECT) scans. Further, the image data 114 may include data identifying the source of the image data 114 such as, but not limited to, patient name, patient age, sex of the patient, patient medical history including prior images of the patient, the area of imaging (e.g., the left breast), the date of imaging, the location of imaging (e.g., Hospital A), etc. In embodiments of the invention, the imaging device 110 and the user device 120 may be the same device. For example, a medical imaging device may have a computer incorporated into the device or be resident in a computer. While only a single imaging device 110 is illustrated, it can be appreciated that the three-dimensional medical image generation system 100 may include one or more imaging device 110. For example, the three-dimensional medical image generation system 100 may include, but is not limited to, a digital breast tomosynthesis imaging device, and a full-field digital mammography imaging device. The imaging device 110 is described in more detail with reference to FIG. 3.

The image datastore 112 may store the image data 114, i.e. the visual, audio, and/or textual data, captured by the imaging device 110. The image datastore 112 may be any storage media capable of storing data, such as, but not limited to, storage media resident in the imaging device 110, a computer system included in or a server coupled to the imaging device 110, and/or in removeable storage media. For example, the image datastore 112 may be, but is not limited to, a hard drive, a solid state drive, a USB drive, or a memory card, etc. In various embodiments, all or part of the image datastore 112 may be installed and run on the imaging device 110. The image datastore 112 is described in more detail above and with reference to FIG. 3.

The user device 120 may include the user interface 122. In the example embodiment, the user device 120 may be a cellphone, desktop computer, a notebook, a laptop computer, a tablet computer, a thin client, or any other electronic device or computing system capable of storing compiling, and organizing audio, visual, or textual content and receiving and sending that content to and from other computing devices, such as the imaging device 110, and the server 130 via the network 140. While only a single user device 120 is depicted, it can be appreciated that any number of user devices may be part of the three-dimensional medical image generation system 100. In embodiments of the invention, the imaging device 110 and the user device 120 may be the same device. For example, a medical imaging device may have a computer incorporated into the device or be resident in a computer. The user device 120 is described in more detail with reference to FIG. 3.

The user interface 122 includes components used to receive input from a user on the user device 120 and transmit the input to the three-dimensional medical image generation program 136 residing on the server 130, or conversely to receive information from the three-dimensional medical image generation program 136 and display the information to the user on the user device 120. In an example embodiment, the user interface 122 uses a combination of technologies and devices, such as device drivers, to provide a platform to enable users of the user device 120 to interact with the three-dimensional medical image generation program 136. In an example embodiment, the user interface 122 receives input, such as but not limited to, textual, visual or audio input received from a physical input device, such as, but not limited to, a keypad, a mouse, a touchscreen, and/or a microphone, etc.

The server 130 may include the program datastore 132 and the three-dimensional medical image generation program 136. In the example embodiment, the server 130 may be a desktop computer, a notebook, a laptop computer, a tablet computer, a thin client, or any other electronic device or computing system capable of storing, compiling, and organizing, audio, visual, or textual content and receiving and sending that content to and from other computing devices, such as the imaging device 110, and the user device 120 via network 140. In some embodiments, the server 130 includes a collection of devices, or data sources, in order to collect the program data 134. The server 130 is described in more detail with reference to FIG. 3.

The program datastore 132 may store the program data 134. The program datastore 132 may be any storage media capable of storing data, such as, but not limited to, storage media resident in the server 130 and/or removeable storage media. For example, the program datastore 132 may be, but is not limited to, a hard drive, a solid state drive, a USB drive, or a memory card, etc. In various embodiments, all or part of the program datastore 132 may be installed and run on the server 130. The program datastore 132 is described in more detail below and with reference to FIG. 3.

The program data 134 may be a collection of audiovisual content required by the three-dimensional medical image generation program 136 including, but not limited to, audio, visual and textual content. The program data 134 may be, for example, but not limited to, the image data 114 received and/or collected from the imaging device 110 and the user device 120. Further, the program data 134 may include, but is not limited to, user data, patient data, imaging studies, and medical reports, etc. The program data 134 is located on the server 130 and can be accessed via the network 140. In accordance with an embodiment of the invention, the program data 134 may be located on one or more of a plurality of servers 130.

The three-dimensional medical image generation program 136 is a program capable of receiving the image data 114 from the imaging device 110 and/or the user device 120 and generating a new three-dimensional medial image of a patient (which may be referred to as a first patient) corresponding to one or more previous two-dimensional medical images of the first patient. The three-dimensional medical image generation program 136 may generate the new three-dimensional medical image by inputting a current three-dimensional medical image of the first patient, one or more past two-dimensional medical images of the first patient, and a plurality of three-dimensional medical images of one or more second patients into a generative adversarial network (GAN). Thus, the three-dimensional medical image generation program 136 produces a three-dimensional medical image representing a prior two-dimensional medical image of the first patient. The three-dimensional medical image generation program 136 may compare the generated three-dimensional image to another three-dimensional image of the same patient to detect any changes and/or differences. The three-dimensional medical image generation program 136 is described in more detail below with reference to FIG. 1b.

Figure 1B:
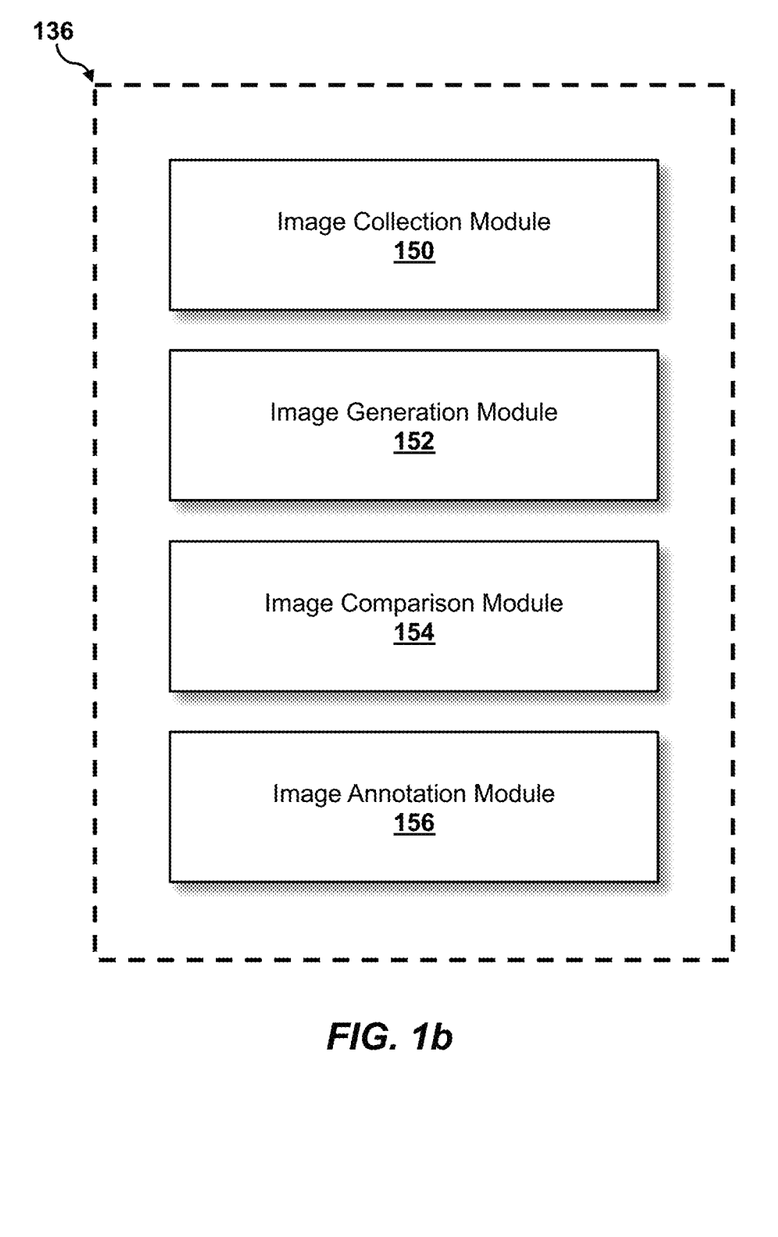

FIG. 1b illustrates example modules of the three-dimensional medical image generation program 136. In an example embodiment, the three-dimensional medical image generation program 136 may include four modules: the image collection module 150, the image generation module 152, the image comparison module 154, and the image annotation module 156.

The image collection module 150 receives the image data 114 captured from the imaging device 110. In an embodiment of the invention, the image data 114 may be sent to the three-dimensional medical image generation program 136 residing on the server 130 by the user device 120 via the user interface 122 or the image data 114 may be sent directly to the three-dimensional medical image generation program 136 residing on the server 130 by the imaging device 110. In an alternative embodiment of the invention, the image data 114 may be collected by the user device 120 and then sent to the server 130 using the network 140 or the image data 114 may be collected directly from the imaging device 110 by the server 130 using the network 140. In embodiments of the invention, the image collection module 150 may receive medical images for a first patient such as, but not limited to, one or more three-dimensional medical images from a first period of time, and one or more two-dimensional medical images from a second period of time. For example, the image collection module 150 may receive a current digital breast tomosynthesis (DBT) exam of a first patient and a past full-field digital mammography (FFDM) exam of a first patient. A DBT exam may contain two three-dimensional image volumes with the first image volume corresponding to a first breast, e.g. the left breast, of the first patient and the second image volume corresponding to a second breast, e.g. a right breast, of the first patient. An FFDM exam may contain a two-dimensional craniocaudal view image of the first breast of the first patient, a two-dimensional mediolateral oblique view image of the first breast of the first patient, a two-dimensional craniocaudal view image of the second breast of the first patient, and a two-dimensional mediolateral oblique view image of the second breast of the first patient. Further, the image collection module 150 may receive medical images from a plurality of second patients such as, but not limited to, a plurality of DBT exams for the plurality of second patients. In an embodiment of the invention, the image data 114 may be stored in the program data 134 of the program datastore 132. For example, the image collection module 150 may receive two-dimensional medical images of a first patient, e.g. an FFDM exam, three-dimensional medical images of a first patient, e.g. a DBT exam, and a plurality of three-dimensional medical images of a plurality of second patients, e.g. DBT exams, and store those medical images on the program datastore 132 of the server 130. While the previous example utilizes DBT exams and FFDM exams, which may contain images corresponding to two body parts, e.g. the left and right breasts of a patient, it can be appreciated that the three-dimensional medical image generation program 136 may only receive a single three-dimensional medical image corresponding to a single body part of a first patient and a single two-dimensional medical image corresponding to the same body part of the first patient.

The image generation module 152 inputs the received image data 114 into a generative adversarial network (GAN). GANs are machine learning systems which utilize two neural networks that compete with each other. A generative neural network generates new data instances while a discriminative neural network evaluates the generated data instances for authenticity. The goal of the generative network is to generate data instances that will be deemed authentic by the discriminative network. The goal of the discriminative network is to recognize data instances generated by the generative network that are not authentic. When a data instance is input to the discriminative network it outputs a probability, e.g., a number between 0 and 1, that the data instance is authentic. GANs are trained with a training set. After successful training, a GAN is able to generate new data with the same statistical properties as the training set. For example, a GAN may be given a training set of images, e.g., image data 114 and after successful training on the training set of images, the GAN is able to generate images that appear to a human observer as authentic as the training set images. In embodiments of the invention, the image generation module 152 inputs a current DBT exam, e.g. three-dimensional medical images, of a first patient, a past FFDM exam, e.g. two-dimensional medical images, of the first patient, and a plurality of DBT exams, e.g. three-dimensional medical images, of a plurality of second patients into a GAN. The image generation module 152 generates a synthetic DBT exam, e.g., a three-dimensional medical image, corresponding to the past FFDM exam, e.g., two-dimensional medical images, of the first patient utilizing the GAN. The synthetic three-dimensional medical image corresponding to the past FFDM exam is then input into a first discriminator of the GAN. The first discriminator tries to discriminate between the generated synthetic three-dimensional medical image and the plurality of three-dimensional medical images from the plurality of second patients. Further, the synthetic three-dimensional medical image corresponding to the past FFDM exam is then input into a second discriminator of the GAN. The second discriminator creates projected two-dimensional medical images, e.g., FFDM images, and the GAN tries to discriminate between the projected two-dimensional medical images and the received two-dimensional medical images of the first patient, e.g., the FFDM of the first patient. While the previous example utilizes DBT exams and FFDM exams, which may contain images corresponding to two body parts, e.g., the left and right breasts of a patient, it can be appreciated that the three-dimensional medical image generation program 136 may only input a single three-dimensional medical image corresponding to a single body part of a first patient and a single two-dimensional medical image corresponding to the same body part of the first patient into the GAN. Further, it can be appreciated that the image generation module 152 may generate a single synthetic three-dimensional medical image of a body part of the first patient corresponding to a past two-dimensional medical image of the same body part of the first patient.

The image comparison module 154 analyzes the synthetic three-dimensional medical image of the first patient for one or more differences compared to a three-dimensional medical image of the first patient received as part of the image data 114. In an embodiment of the invention, the image comparison module 154 would compare a synthetic DBT exam, e. gthe synthetic three-dimensional medical image, of the first patient to the most current three-dimensional medical image of the first patient, e.g., the current DBT exam. For example, the synthetic three-dimensional medical image of the first patient would correspond to a past medical exam of the patient as it was generated from an older technology, e.g., from two-dimensional medical images. Thus, the image comparison module 154 detects the differences between the most recent medical image of the first patient, e.g. the current DBT exam, and a previous medical image of the first patient, e.g. the synthetic three-dimensional medical image.

The image comparison module 154 may utilize any image recognition technology to compare the medical images such as, but not limited to, deep learning algorithms, and/or a deep neural network, e.g., a deep convolutional neural network. Deep convolutional neural networks are a class of deep, feed-forward artificial neural networks consisting of an input layer, an output layer, and multiple hidden layers used to analyze images. An example image recognition technology utilized by the image comparison module 154 may be, but is not limited to, the IBM Watson™ Visual Recognition Service which uses deep learning algorithms to analyze images for scenes, objects, and other content. Optionally, or additionally, the synthetic three-dimensional medical image of the first patient may be analyzed by a human.

The image annotation module 156 annotates the three-dimensional medical image of the first patient received as part of the image data 114, e.g. the current DBT exam. The image annotation module 156 may annotate the three-dimensional medical image of the first patient with indicators indicating the differences between the first three-dimensional medical image of the first patient and the synthetic three-dimensional image of the first patient. The indicators may include, but are not limited to, arrows, circles, boxes, measurements, and text, etc. For example, the image annotation module 156 may annotate a current DBT exam of a first patient based on the differences detected from the synthetic DBT exam. The differences may include tissue abnormalities detected such as, but not limited to, abnormal tissue masses, lesions, calcifications. Further annotations may include measurements associated with the tissue abnormalities detected such as, but not limited to, mass size, mass density, lesion size, lesion volume, etc. In an embodiment of the invention, the image annotation module 156 generates a textual report describing the differences between the first three-dimensional medical image of the first patient and the synthetic three-dimensional image of the first patient. The image annotation module 156 displays the annotated three-dimensional medical image of the first patient and/or the generated textual report to a user on the user device 120 via the user interface 122.

Figure 2:
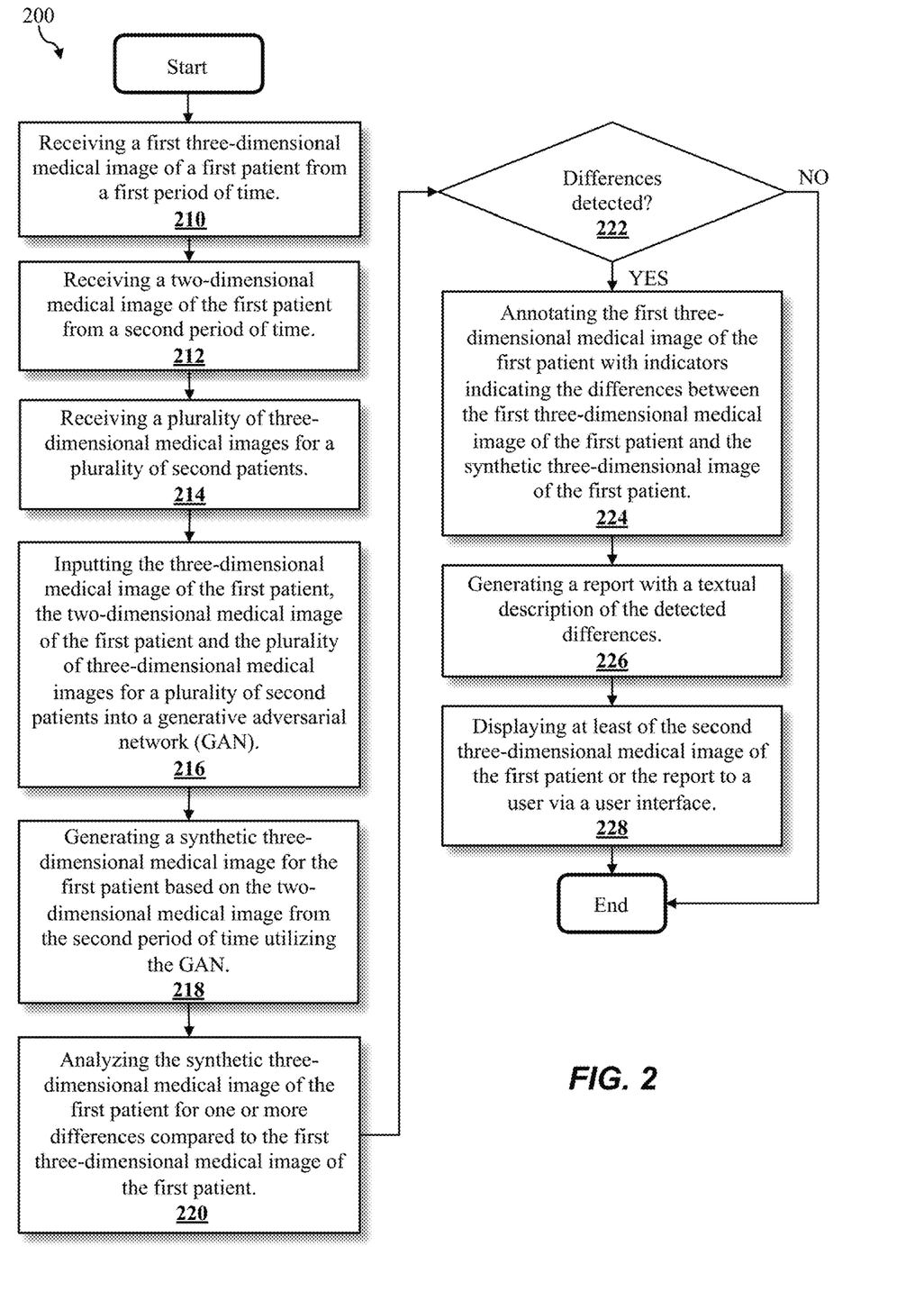
FIG. 2 is a flowchart illustrating an example method of three-dimensional medical image generation in accordance with an embodiment of the invention.

Referring to FIG. 2, a method 200 for three-dimensional medical image generation is depicted in accordance with an embodiment of the present invention.

Referring to block 210, the three-dimensional medical image generation program 136 receives a first three-dimensional medical image of a first patient from a first period of time as part of the image data 114. Image collection is described in more detail above with reference to the image collection module 150 of FIG. 1b.

Referring to block 212, the three-dimensional medical image generation program 136 receives a two-dimensional medical image of the first patient from a second period of time as part of the image data 114. Image collection is described in more detail above with reference to the image collection module 150 of FIG. 1b.

Referring to block 214, the three-dimensional medical image generation program 136 receives a plurality of three-dimensional medical images for a plurality of second patients as part of the image data 114. Image collection is described in more detail above with reference to the image collection module 150 of FIG. 1b.

Referring to block 216, the three-dimensional medical image generation program 136 inputs the three-dimensional medical image of a first patient, the two-dimensional medical image of the first patient and the plurality of three-dimensional medical images for a plurality of second patients into a generative adversarial network. Image input is described in more detail above with reference to the image generation module 152 of FIG. 1*b*.

Referring to block 218, the three-dimensional medical image generation program 136 generates a synthetic three-dimensional medical image for the first patient based on the two-dimensional medical image from the second period of time. Image generation is described in more detail above with reference to the image generation module 152 of FIG. 1*b*.

Referring to block 220, the three-dimensional medical image generation program 136 analyzes the synthetic three-dimensional medical image of the first patient for one or more differences compared to the first three-dimensional medical image of the first patient. Image analysis is described in more detail above with reference to the image comparison module 154 of FIG. 1*b*.

Referring to block 222, if the three-dimensional medical image generation program 136 detects one or more differences between the synthetic three-dimensional medical image of the first patient and the first three-dimensional medical image of the first patient, the three-dimensional medical image generation program 136 proceeds to block 224. If the three-dimensional medical image generation program 136 does not detect one or more differences between the synthetic three-dimensional medical image of the first patient and the first three-dimensional medical image of the first patient, the three-dimensional medical image generation program 136 terminates.

Referring to block 224, the three-dimensional medical image generation program 136 annotates the first three-dimensional medical image of the first patient with indicators indicating the differences between the first three-dimensional medical image of the first patient and the synthetic three-dimensional image of the first patient. Image annotation is described in more detail above with reference to the image annotation module 156 of FIG. 1*b*.

Referring to block 226, the three-dimensional medical image generation program 136 generates a report with a textual description of the detected differences. Report generation is described in more detail above with reference to the image annotation module 156 of FIG. 1*b*.

Referring to block 228, the three-dimensional medical image generation program 136 displays at least one of the second three-dimensional medical image of the first patient or the report to a user via a user interface. Image and/or report display is described in more detail above with reference to the image annotation module 156 of FIG. 1*b*.

Figure 3:
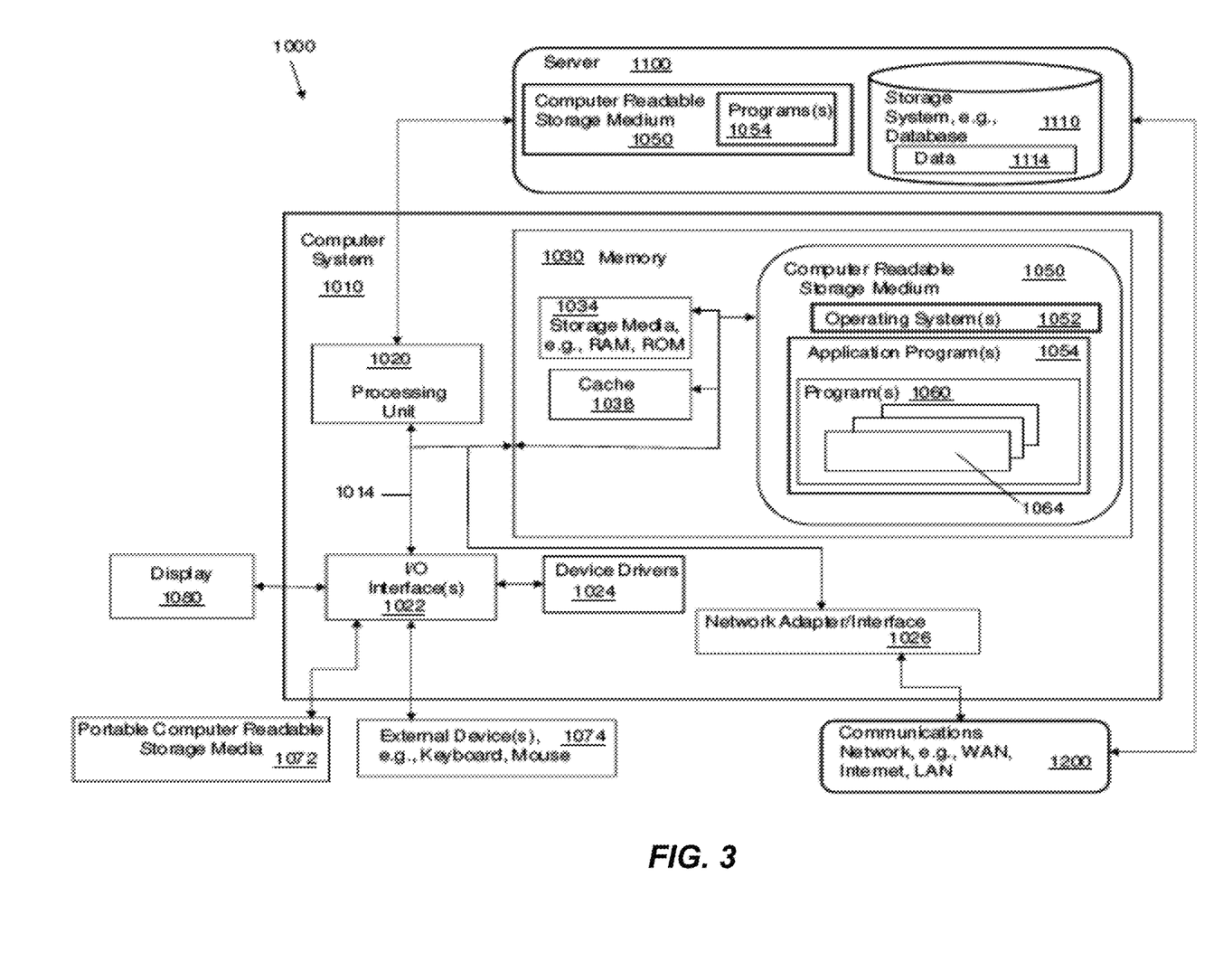
FIG. 3 is a block diagram depicting the hardware components of the three-dimensional medical image generation system of FIG. 1, in accordance with an embodiment of the invention.

Referring to FIG. 3, a system 1000 includes a computer system or computer 1010 shown in the form of a generic computing device. The method 200, for example, may be embodied in a program(s) 1060 (FIG. 3) embodied on a computer readable storage device, for example, generally referred to as memory 1030 and more specifically, computer readable storage medium 1050 as shown in FIG. 3. For example, memory 1030 can include storage media 1034 such as RAM (Random Access Memory) or ROM (Read Only Memory), and cache memory 1038. The program 1060 is executable by the processing unit or processor 1020 of the computer system 1010 (to execute program steps, code, or program code). Additional data storage may also be embodied as a database 1110 which can include data 1114. The computer system 1010 and the program 1060 shown in FIG. 3 are generic representations of a computer and program that may be local to a user, or provided as a remote service (for example, as a cloud based service), and may be provided in further examples, using a web site accessible using the communications network 1200 (e.g., interacting with a network, the Internet, or cloud services). It is understood that the computer system 1010 also generically represents herein a computer device or a computer included in a device, such as a laptop or desktop computer, etc., or one or more servers, alone or as part of a datacenter. The computer system can include a network adapter/interface 1026, and an input/output (I/O) interface(s) 1022. The I/O interface 1022 allows for input and output of data with an external device 1074 that may be connected to the computer system. The network adapter/interface 1026 may provide communications between the computer system a network generically shown as the communications network 1200.

The computer 1010 may be described in the general context of computer system-executable instructions, such as program modules, being executed by a computer system. Generally, program modules may include routines, programs, objects, components, logic, data structures, and so on that perform particular tasks or implement particular abstract data types. The method steps and system components and techniques may be embodied in modules of the program 1060 for performing the tasks of each of the steps of the method and system. The modules are generically represented in FIG. 3 as program modules 1064. The program 1060 and program modules 1064 can execute specific steps, routines, sub-routines, instructions or code, of the program.

The methods of the present disclosure can be run locally on a device such as a mobile device, or can be run a service, for instance, on the server 1100 which may be remote and can be accessed using the communications network 1200. The program or executable instructions may also be offered as a service by a provider. The computer 1010 may be practiced in a distributed cloud computing environment where tasks are performed by remote processing devices that are linked through a communications network 1200. In a distributed cloud computing environment, program modules may be located in both local and remote computer system storage media including memory storage devices.

More specifically, as shown in FIG. 3, the system 1000 includes the computer system 1010 shown in the form of a general-purpose computing device with illustrative periphery devices. The components of the computer system 1010 may include, but are not limited to, one or more processors or processing units 1020, a system memory 1030, and a bus 1014 that couples various system components including system memory 1030 to processor 1020.

The bus 1014 represents one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnects (PCI) bus.

The computer 1010 can include a variety of computer readable media. Such media may be any available media that is accessible by the computer 1010 (e.g., computer system, or server), and can include both volatile and non-volatile media, as well as, removable and non-removable media. Computer memory 1030 can include additional computer readable media 1034 in the form of volatile memory, such as random access memory (RAM), and/or cache memory 1038. The computer 1010 may further include other removable/non-removable, volatile/non-volatile computer storage media, in one example, portable computer readable storage media 1072. In one embodiment, the computer readable storage medium 1050 can be provided for reading from and writing to a non-removable, non-volatile magnetic media. The computer readable storage medium 1050 can be embodied, for example, as a hard drive. Additional memory and data storage can be provided, for example, as the storage system 1110 (e.g., a datastore such as the image datastore 112 or the program datastore 132) for storing data 1114, e.g. image data 114 or the program data 134, and communicating with the processing unit 1020. The database can be stored on or be part of a server 1100. Although not shown, a magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media can be provided. In such instances, each can be connected to bus 1014 by one or more data media interfaces. As will be further depicted and described below, memory 1030 may include at least one program product which can include one or more program modules that are configured to carry out the functions of embodiments of the present invention. As such, the computing device in FIG. 3 becomes specifically configured to implement mechanisms of the illustrative embodiments and specifically configured to perform the operations and generated the outputs of described herein for determining a route based on a user's preferred environmental experiences.

The method 200 (FIG. 2), for example, may be embodied in one or more computer programs, generically referred to as a program(s) 1060 and can be stored in memory 1030 in the computer readable storage medium 1050. The program 1060 can include program modules 1064. The program modules 1064 can generally carry out functions and/or methodologies of embodiments of the invention as described herein. For example, the program modules 1064 can include the modules 150-156 described above with reference to FIG. 1*b*. The one or more programs 1060 are stored in memory 1030 and are executable by the processing unit 1020. By way of example, the memory 1030 may store an operating system 1052, one or more application programs 1054, other program modules, and program data on the computer readable storage medium 1050. It is understood that the program 1060, and the operating system 1052 and the application program(s) 1054 stored on the computer readable storage medium 1050 are similarly executable by the processing unit 1020.

The computer 1010 may also communicate with one or more external devices 1074 such as a keyboard, a pointing device, a display 1080, etc.; one or more devices that enable a user to interact with the computer 1010; and/or any devices (e.g., network card, modem, etc.) that enables the computer 1010 to communicate with one or more other computing devices. Such communication can occur via the Input/Output (I/O) interfaces 1022. Still yet, the computer 1010 can communicate with one or more networks 1200 such as a local area network (LAN), a general wide area network (WAN), and/or a public network (e.g., the Internet) via network adapter/interface 1026. As depicted, network adapter 1026 communicates with the other components of the computer 1010 via bus 1014. It should be understood that although not shown, other hardware and/or software components could be used in conjunction with the computer 1010. Examples, include, but are not limited to: microcode, device drivers 1024, redundant processing units, external disk drive arrays, RAID systems, tape drives, and data archival storage systems, etc.

It is understood that a computer or a program running on the computer 1010 may communicate with a server, embodied as the server 1100, via one or more communications networks, embodied as the communications network 1200. The communications network 1200 may include transmission media and network links which include, for example, wireless, wired, or optical fiber, and routers, firewalls, switches, and gateway computers. The communications network may include connections, such as wire, wireless communication links, or fiber optic cables. A communications network may represent a worldwide collection of networks and gateways, such as the Internet, that use various protocols to communicate with one another, such as Lightweight Directory Access Protocol (LDAP), Transport Control Protocol/Internet Protocol (TCP/IP), Hypertext Transport Protocol (HTTP), Wireless Application Protocol (WAP), etc. A network may also include a number of different types of networks, such as, for example, an intranet, a local area network (LAN), or a wide area network (WAN).

In one example, a computer can use a network which may access a website on the Web (World Wide Web) using the Internet. In one embodiment, a computer 1010, including a mobile device, can use a communications system or network 1200 which can include the Internet, or a public switched telephone network (PSTN) for example, a cellular network. The PSTN may include telephone lines, fiber optic cables, microwave transmission links, cellular networks, and communications satellites. The Internet may facilitate numerous searching and texting techniques, for example, using a cell phone or laptop computer to send queries to search engines via text messages (SMS), Multimedia Messaging Service (MMS) (related to SMS), email, or a web browser. The search engine can retrieve search results, that is, links to websites, documents, or other downloadable data that correspond to the query, and similarly, provide the search results to the user via the device as, for example, a web page of search results.

It is to be understood that although this disclosure includes a detailed description on cloud computing, implementation of the teachings recited herein are not limited to a cloud computing environment. Rather, embodiments of the present invention are capable of being implemented in conjunction with any other type of computing environment now known or later developed.

Cloud computing is a model of service delivery for enabling convenient, on-demand network access to a shared pool of configurable computing resources (e.g., networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics are as follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported, providing transparency for both the provider and consumer of the utilized service.

Service Models are as follows:

Software as a Service (SaaS): the capability provided to the consumer is to use the provider's applications running on a cloud infrastructure. The applications are accessible from various client devices through a thin client interface such as a web browser (e.g., web-based e-mail). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

A cloud computing environment is service oriented with a focus on statelessness, low coupling, modularity, and semantic interoperability. At the heart of cloud computing is an infrastructure that includes a network of interconnected nodes.

Figure 4:
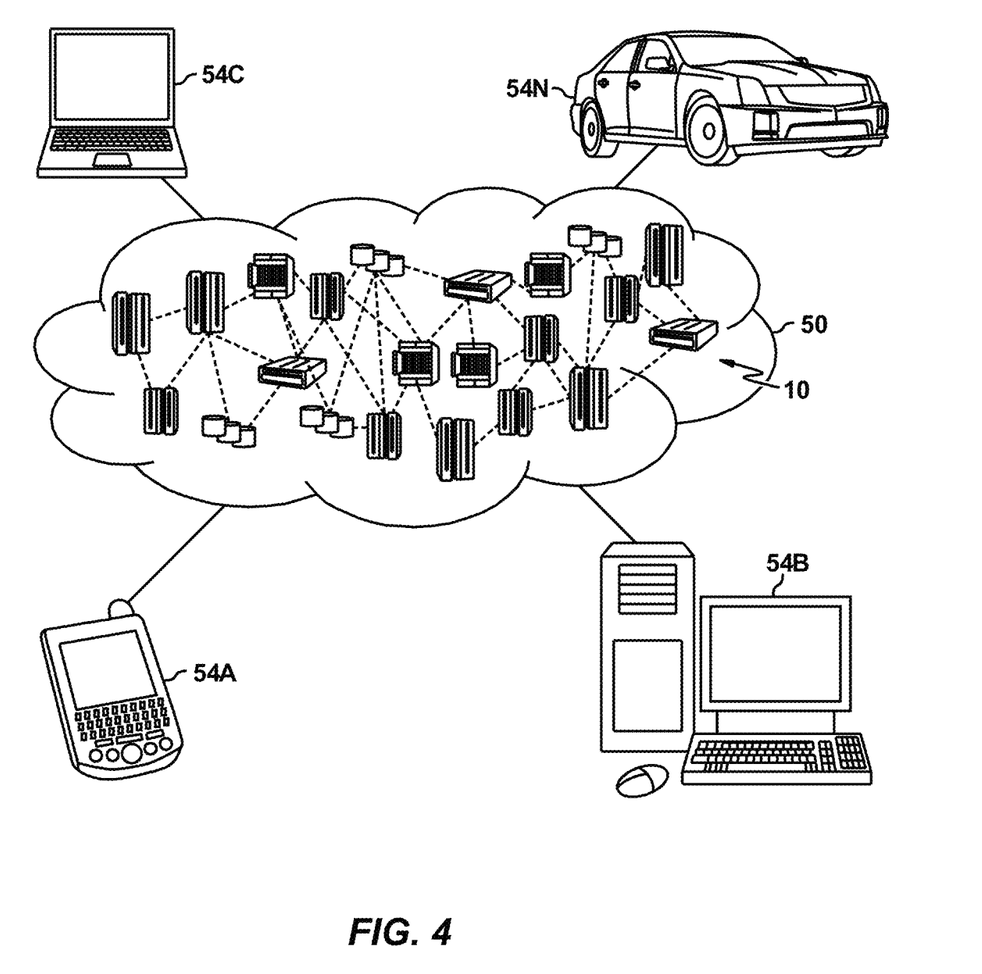
FIG. 4 illustrates a cloud computing environment, in accordance with an embodiment of the invention.

Referring now to FIG. 4, illustrative cloud computing environment 50 is depicted. As shown, cloud computing environment 50 includes one or more cloud computing nodes 10 with which local computing devices used by cloud consumers, such as, for example, personal digital assistant (PDA) or cellular telephone 54A, desktop computer 54B, laptop computer 54C, and/or automobile computer system 54N may communicate. Nodes 10 may communicate with one another. They may be grouped (not shown) physically or virtually, in one or more networks, such as Private, Community, Public, or Hybrid clouds as described hereinabove, or a combination thereof. This allows cloud computing environment 50 to offer infrastructure, platforms and/or software as services for which a cloud consumer does not need to maintain resources on a local computing device. It is understood that the types of computing devices 54A-N shown in FIG. 4 are intended to be illustrative only and that computing nodes 10 and cloud computing environment 50 can communicate with any type of computerized device over any type of network and/or network addressable connection (e.g., using a web browser).

Figure 5:
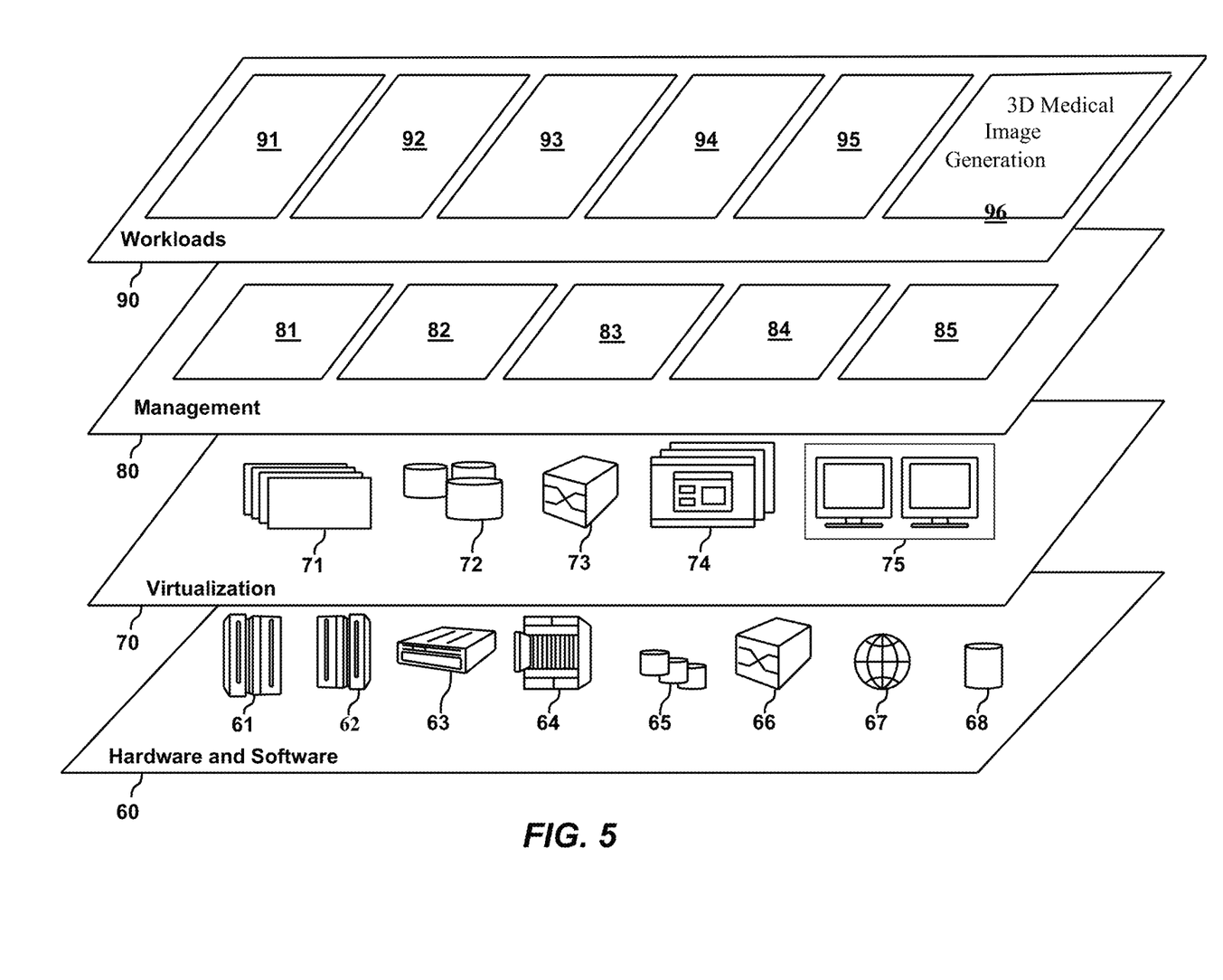
FIG. 5 illustrates a set of functional abstraction layers provided by the cloud computing environment of FIG. 4, in accordance with an embodiment of the invention.

Referring now to FIG. 5, a set of functional abstraction layers provided by cloud computing environment 50 (FIG. 4) is shown. It should be understood in advance that the components, layers, and functions shown in FIG. 5 are intended to be illustrative only and embodiments of the invention are not limited thereto. As depicted, the following layers and corresponding functions are provided:

Hardware and software layer 60 includes hardware and software components. Examples of hardware components include: mainframes 61; RISC (Reduced Instruction Set Computer) architecture based servers 62; servers 63; blade servers 64; storage devices 65; and networks and networking components 66. In some embodiments, software components include network application server software 67 and database software 68.

Virtualization layer 70 provides an abstraction layer from which the following examples of virtual entities may be provided: virtual servers 71; virtual storage 72; virtual networks 73, including virtual private networks; virtual applications and operating systems 74; and virtual clients 75.

In one example, management layer 80 may provide the functions described below. Resource provisioning 81 provides dynamic procurement of computing resources and other resources that are utilized to perform tasks within the cloud computing environment. Metering and Pricing 82 provide cost tracking as resources are utilized within the cloud computing environment, and billing or invoicing for consumption of these resources. In one example, these resources may include application software licenses. Security provides identity verification for cloud consumers and tasks, as well as protection for data and other resources. User portal 83 provides access to the cloud computing environment for consumers and system administrators. Service level management 84 provides cloud computing resource allocation and management such that required service levels are met. Service Level Agreement (SLA) planning and fulfillment 85 provide pre-arrangement for, and procurement of, cloud computing resources for which a future requirement is anticipated in accordance with an SLA.

Workloads layer 90 provides examples of functionality for which the cloud computing environment may be utilized. Examples of workloads and functions which may be provided from this layer include: mapping and navigation 91; software development and lifecycle management 92; virtual classroom education delivery 93; data analytics processing 94; transaction processing 95; and three-dimensional medical image generation 96.

The programs described herein are identified based upon the application for which they are implemented in a specific embodiment of the invention. However, it should be appreciated that any particular program nomenclature herein is used merely for convenience, and thus the invention should not be limited to use solely in any specific application identified and/or implied by such nomenclature.

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

While steps of the disclosed method and components of the disclosed systems and environments have been sequentially or serially identified using numbers and letters, such numbering or lettering is not an indication that such steps must be performed in the order recited, and is merely provided to facilitate clear referencing of the method's steps. Furthermore, steps of the method may be performed in parallel to perform their described functionality.

What is claimed is:

1. A method for three-dimensional medical image generation, the method comprising:
    receiving a first three-dimensional medical image, that was taken from a first patient at a first period of time;
    receiving a two-dimensional medical image, that was taken from the first patient at a second period of time;
    receiving a plurality of three-dimensional medical images for a plurality of second patients;
    inputting the first three-dimensional medical image of the first patient, the two-dimensional medical image of the first patient, and the plurality of three-dimensional medical images for the plurality of second patients into a generative adversarial network (GAN); and
    generating a synthetic three-dimensional medical image for the first patient based on the two-dimensional medical image from the second period of time utilizing the GAN.

2. The method of claim 1, further comprising:
    analyzing the synthetic three-dimensional medical image of the first patient for one or more differences compared to the first three-dimensional medical image of the first patient; and
    annotating the three-dimensional medical image of the first patient with indicators indicating the differences between the first three-dimensional medical image of the first patient and the synthetic three-dimensional image of the first patient.

3. The method of claim 2, further comprising:
    generating a report with a textual description of the differences; and
    displaying at least one of the synthetic three-dimensional medical image of the first patient, the report, and the annotated three-dimensional medical image of the first patient to a user via a user interface.

4. The method of claim 1, wherein the first three-dimensional medical image of the first patient is a digital breast tomosynthesis (DBT) image.

5. The method of claim 1, wherein the two-dimensional medical image is a full-field digital mammography (FFDM) image.

6. The method of claim 1, wherein the plurality of three-dimensional images for the plurality of second patients are digital breast tomosynthesis (DBT) images.

7. The method of claim 1, wherein generating the synthetic three-dimensional medical image for the first patient based on the two-dimensional medical image from the second period of time utilizing the GAN further comprises:
    inputting the synthetic three-dimensional medical image into a first discriminator of the GAN, wherein the first discriminator tries to discriminate between the synthetic three-dimensional medical image and the plurality of three-dimensional medical images from the plurality of second patients; and
    inputting the synthetic three-dimensional medical image into a second discriminator of the GAN, wherein the second discriminator creates projected two-dimensional medical images corresponding to the synthetic three-dimensional medical image, wherein the second discriminator tries to discriminate between the projected two-dimensional medical images corresponding to the synthetic three-dimensional medical image and the two-dimensional medical image of the first patient from the second period of time.

8. A computer program product for three-dimensional medical image generation, the computer program product comprising:
    a computer-readable storage medium having program instructions embodied therewith, wherein the computer readable storage medium is not a transitory signal per se, wherein the program instructions are executable by a computer to cause the computer to perform a method, the method comprising:
        receiving a first three-dimensional medical image, that was taken from a first patient at a first period of time;
        receiving a two-dimensional medical image, that was taken from the first patient at a second period of time;
        receiving a plurality of three-dimensional medical images for a plurality of second patients;
        inputting the first three-dimensional medical image of the first patient, the two-dimensional medical image of the first patient and the plurality of three-dimensional medical images for the plurality of second patients into a generative adversarial network (GAN); and
        generating a synthetic three-dimensional medical image for the first patient based on the two-dimensional medical image from the second period of time utilizing the GAN.

9. The computer program product of claim 8, further comprising:
    analyzing the synthetic three-dimensional medical image of the first patient for one or more differences compared to the first three-dimensional medical image of the first patient; and
    annotating the three-dimensional medical image of the first patient with indicators indicating the differences between the first three-dimensional medical image of the first patient and the synthetic three-dimensional image of the first patient.

10. The computer program product of claim 9, further comprising:
    generating a report with a textual description of the differences; and
    displaying at least one of the synthetic three-dimensional medical image of the first patient, the report, and the annotated three-dimensional medical image of the first patient to a user via a user interface.

11. The computer program product of claim 8, wherein the first three-dimensional medical image of the first patient is a digital breast tomosynthesis (DBT) image.

12. The computer program product of claim 8, wherein the two-dimensional medical image is a full-field digital mammography (FFDM) image.

13. The computer program product of claim 8, wherein the plurality of three-dimensional images for the plurality of second patients are digital breast tomosynthesis (DBT) images.

14. The computer program product of claim 8, wherein generating the synthetic three-dimensional medical image for the first patient based on the two-dimensional medical image from the second period of time utilizing the GAN further comprises:
  inputting the synthetic three-dimensional medical image into a first discriminator of the GAN, wherein the first discriminator tries to discriminate between the synthetic three-dimensional medical image and the plurality of three-dimensional medical images from the plurality of second patients; and
  inputting the synthetic three-dimensional medical image into a second discriminator of the GAN, wherein the second discriminator creates projected two-dimensional medical images corresponding to the synthetic three-dimensional medical image, wherein the second discriminator tries to discriminate between the projected two-dimensional medical images corresponding to the synthetic three-dimensional medical image and the two-dimensional medical image of the first patient from the second period of time.

15. A system for three-dimensional medical image generation, the system comprising:
  a computer system comprising: a processor, a computer readable storage medium, and program instructions stored on the computer readable storage medium that are executable by the processor to cause the computer system to:
  receive a first three-dimensional medical image, that was taken from a first patient at a first period of time;
  receive a two-dimensional medical image, that was taken from the first patient at a second period of time;
  receive a plurality of three-dimensional medical images for a plurality of second patients;
  input the first three-dimensional medical image of the first patient, the two-dimensional medical image of the first patient and the plurality of three-dimensional medical images for the plurality of second patients into a generative adversarial network (GAN); and
  generate a synthetic three-dimensional medical image for the first patient based on the two-dimensional medical image from the second period of time utilizing the GAN.

16. The system of claim 15, further comprising program instructions to:
  analyze the synthetic three-dimensional medical image of the first patient for one or more differences compared to the first three-dimensional medical image of the first patient; and
  annotate the three-dimensional medical image of the first patient with indicators indicating the differences between the first three-dimensional medical image of the first patient and the synthetic three-dimensional image of the first patient.

17. The system of claim 16, further comprising program instructions to:
  generate a report with a textual description of the differences; and
  display at least one of the second three-dimensional medical image of the first patient, the report, and the annotated three-dimensional medical image of the first patient to a user via a user interface.

18. The system of claim 15, wherein the first three-dimensional medical image of the first patient and the plurality of three-dimensional images for the plurality of second patients are digital breast tomosynthesis (DBT) images.

19. The system of claim 15, wherein the two-dimensional medical image is a full-field digital mammography (FFDM) image.

20. The system of claim 15, wherein the program instructions to generate the synthetic three-dimensional medical image for the first patient based on the two-dimensional medical image from the second period of time utilizing the GAN further comprise program instructions to:
  input the synthetic three-dimensional medical image into a first discriminator of the GAN, wherein the first discriminator tries to discriminate between the synthetic three-dimensional medical image and the plurality of three-dimensional medical images from the plurality of second patients; and
  input the synthetic three-dimensional medical image into a second discriminator of the GAN, wherein the second discriminator creates projected two-dimensional medical images corresponding to the synthetic three-dimensional medical image, wherein the second discriminator tries to discriminate between the projected two-dimensional medical images corresponding to the synthetic three-dimensional medical image and the two-dimensional medical image of the first patient from the second period of time.

* * * * *